United States Patent [19]

Hinsken et al.

[11] 4,407,993

[45] Oct. 4, 1983

[54] HINDERED PIPERIDINE POLYMER STABILIZERS

[75] Inventors: Hans Hinsken, Kandern, Fed. Rep. of Germany; Wolfgang Mueller, Allschwil, Switzerland; Hermann Schneider, Grenzach-Wyhlen, Fed. Rep. of Germany

[73] Assignee: Sandoz Ltd., Basel, Switzerland

[21] Appl. No.: 357,886

[22] Filed: Mar. 15, 1982

[30] Foreign Application Priority Data

Mar. 20, 1981 [DE] Fed. Rep. of Germany ....... 3110969

[51] Int. Cl.$^3$ ..................... C08K 5/34; C07D 211/44; C08K 5/35
[52] U.S. Cl. ................... 524/96; 324/99 R; 324/100; 544/129; 544/130; 544/217; 546/188; 546/187; 546/201; 546/208; 546/216; 546/222; 546/242

[58] Field of Search ........................ 524/96, 99, 100; 544/129, 130, 217; 546/187, 188, 201, 208, 222, 216, 242

[56] References Cited

U.S. PATENT DOCUMENTS 4,014,887  3/1977  Randall et al. ...................... 546/188
4,256,627  3/1981  Moser et al. ........................... 546/19

FOREIGN PATENT DOCUMENTS 2352658  4/1974  Fed. Rep. of Germany ...... 546/242

Primary Examiner—Robert T. Bond
Attorney, Agent, or Firm—Gerald D. Sharkin; Richard E. Vila; Frederick H. Weinfeldt

[57] ABSTRACT

N-($\beta$-aminoethyl)-3-hydroxy-1,1,6,6-tetramethylpiperidine and certain of its N- and —O- substituted derivatives are useful as light stabilizers for polymeric materials, particularly for thermoplastic polymers and automotive finishes. Preferred compounds include the N-, O-diacyl derivatives.

13 Claims, No Drawings

HINDERED PIPERIDINE POLYMER STABILIZERS

This invention relates to N-($\beta$-aminoethyl)tetramethylpiperidines, which are useful as light stabilizers for polymeric materials.

The invention provides compounds of formula I

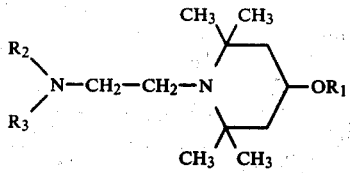  I in which $R_1$ is hydrogen or a group

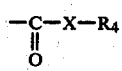  (a)

in which X is a direct bond, —O— or —NH—; and $R_4$ is $C_{1-18}$alkyl, $C_{5-8}$cycloalkyl, phenyl$(C_{1-4})$alkyl, phenyl, phenyl substituted with 1 or 2 $C_{1-12}$alkyl groups having together no more than 18 carbon atoms, or the group

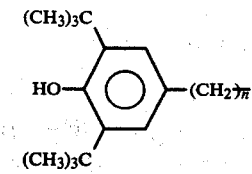  (e)

in which n=0, 1 or 2, or, when X is —NH—, $R_4$ may also be $C_{1-18}$alkyl monosubstituted by isocyanate $R_2$ is hydrogen, $C_{1-18}$alkyl or a group (a); and
$R_3$ is hydrogen, $C_{1-18}$alkyl or a group (b), (c) or (d)

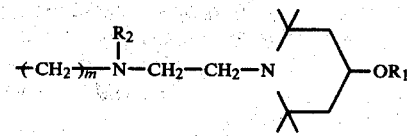  (b)

in which m is 2–10 and $R_1$ and $R_2$ are as defined above,

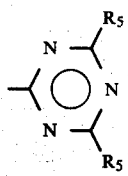  (c)

in which each $R_5$ independently is chlorine;

—$NR_7R_8$  (f)

in which
$R_7$ is hydrogen, $C_{1-18}$alkyl or $\beta$-hydroxyethyl and
$R_8$ is $C_{1-18}$alkyl, $\beta$-hydroxyethyl or phenyl or
$R_7$ and $R_8$ together with the nitrogen atom to which they are attached form a piperidine or morpholine ring;

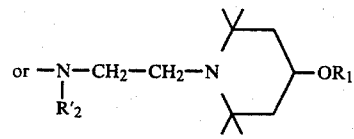  (g)

in which
$R'_2$ is hydrogen or $C_{1-18}$alkyl and
$R_1$ is as defined above;

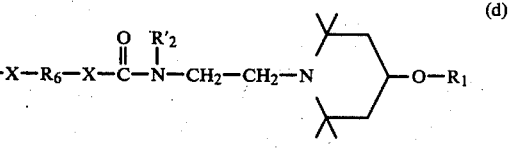  (d)

in which
X, $R_1$ and $R_2'$ are as defined above, and
$R_6$ is $C_{2-10}$alkylene, phenylene, phenylene mono- or di-substituted by $C_{1-9}$alkyl, or, when X is a direct bond, $R_6$ may also be —$CH_2$— or a direct bond, provided that, when $R_3$ is a group (c) or (d) then $R_2$ is $R_2'$; or $R_2$ and $R_3$, together with the nitrogen atom to which they are attached, form a succinimide, maleimide or phthalimide ring.

When any symbol appears more than once in a formula, it may have the same or a different significance, unless otherwise stated. Any groups capable of substitution are unsubstituted unless otherwise stated.

$R_1$ is preferably $R_1'$ where $R_1'$ is hydrogen or a group (a) in which X is X' where X' is a direct bond or —NH—, more preferably hydrogen.

X is preferably X', more preferably a direct bond.

$R_2$ is preferably $R_2'$, more preferably hydrogen or $C_{1-12}$alkyl, particularly hydrogen, except when $R_3$ is hydrogen, in which case $R_2$ is preferably a group (a).

When $R_2$ is $R_2'$, $R_3$ is preferably $R_3'$ where $R_3'$ is $C_{1-18}$alkyl or a group (c) or (d), more preferably $R_3''$ where $R_3''$ is a group (c).

When $R_2$ is a group (a), $R_3$ is preferably hydrogen.

When $R_1$ is a group (a), then $R_3$ is preferably hydrogen and $R_2$ is preferably also a group (a), more preferably both groups (a) being identical, or $R_2$ and $R_3$ together with the nitrogen atom to which they are attached form a succinimide, maleimide or phthalimide ring.

When $R_3$ is a group (b), m is preferably 8 or 10.

$R_4$ is preferably $R_4'$ where $R_4'$ is $C_{1-18}$alkyl, cyclohexyl, benzyl or phenyl, more preferably $C_{1-18}$alkyl. When $R_4$ is a group (e) then n is preferably 0 or 2, more preferably 2.

In group (c), preferably at least one $R_5$ is a group (g). Group (f) is preferably a piperidinyl or morpholinyl group. In group (d), $R_6$ is preferably $C_{4-8}$alkylene or p-phenylene when X is a direct bond, and preferably $C_{4-12}$alkylene, phenylene or phenylene mono- or disubstituted with $C_{1-4}$alkyl, more preferably hexamethylene, when X is —NH—.

Preferred compounds are those of formula

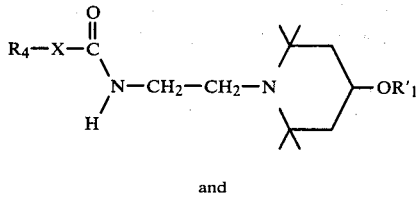

Ia and

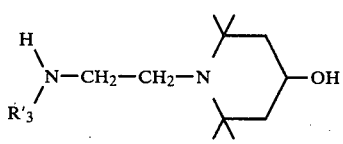

Ib preferred compounds of the type of formula Ia being those of formula

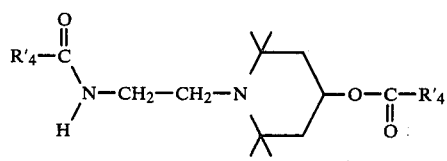

I'a

Compounds of formula I may be prepared via the compound of formula Ic

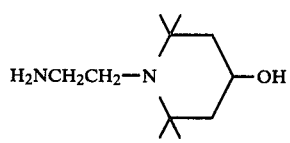

Ic which itself may be prepared by reduction in conventional manner (for example with a metal hydride or by hydrogen in the presence of a catalyst) of the compound of formula II

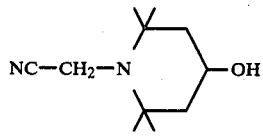

II

The compound of formula II may be prepared by the reaction of 4-hydroxy-2,2,6,6-tetramethylpiperidine with glycollic acid nitrile in aqueous solution. A mixture of acetone cyanhydrin and formaldehyde may be used in place of glycollic acid nitrile. Compound Ic may also be prepared by reduction of the ketone III.

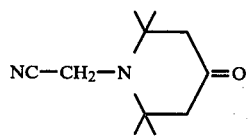

III

The compound of formula Ic may be used to prepare other compounds of formula I by means of conventional reactions, for example:

(i) for $R_2$ and/or $R_3$=alkyl; with an alkylating agent (ii) for $R_1$ and/or $R_2$=—COR$_4$; with a compound R$_4$.COOH or a functional derivative thereof (iii) for $R_1$ and/or $R_2$=—COOR$_4$; with a compound

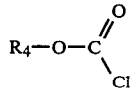

(iv) for $R_1$ and/or $R_2$=—CONHR$_4$; with a compound of formula R$_4$—N=C=O (v) for $R_3$=(b); by reaction of 2 moles Ic with a compound of formula HOOC—CH$_2$)$_p$COOH where p is 0–8, or a functional derivative thereof, and reducing the resulting amide (vi) for $R_3$=(c); with a compound of formula

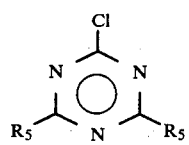

(vii) for $R_3$=(d) in which X is a direct bond; with a compound of formula HOOC.R$_6$.COOH or a functional derivative thereof (viii) for $R_3$ (d) in which X is —O—; with a compound of formula

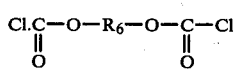

(ix) for $R_3$=(d) in which X is —NH—; with a compound of formula

O=C=N—R$_6$—N=C=O (x) for $R_2$ and $R_3$ together with the nitrogen atom to which they are attached=a succinimide, maleamide or phthalimide ring; with succinic, malic or phthalic anhydride.

Compounds of formula I are useful as stabilizers to protect polymeric materials against degradation by light. The compounds have particularly good solubility and miscibility in solvent systems and in liquid polymers and prepolymers, which makes them useable in a wide range of polymeric materials.

The concentration of compound of formula I employed in the polymeric material is suitably 0.01 to 5% by weight, preferably 0.02 to 1% by weight. The compound may be added before, during or after the polymerization step, and may be added in solid form; in solution, preferably as a liquid concentrate containing from 20–80% by weight of compound of formula I; or as a solid masterbatch composition containing 20–80% by wt. of compound of formula I and 80–20% by wt. of a solid polymeric material which is identical with or compatible with the polymeric material to be stabilized.

Suitable polymeric materials include plastics materials for example polyethylene, polypropylene, ethylene/propylene copolymers, polyvinyl chloride, polyester; polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastics materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastics polymers in the melt, for example in a melt blender or during the formation of shaped articles, including foils, tubes, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples include sterically hindered phenols, sulphur or phosphorus-containing compounds or mixtures of these. Examples are benzofuran-2-ones; indolin-2-ones and sterically hindered phenols such as β-(4-hydroxy-3,5-ditert.-butylphenyl)-propionyl stearate, methane tetrakis-[methylene-3(3′,5′-ditert.-butyl-4-hydroxyphenyl-)-propionate], 1,3,3-tris-(2-methyl-4-hydroxy-5-tert.-butylphenyl)-butane, 1,3,5-tris(4-tert.-butyl-3-hydroxy-2,6-dimethylbenzyl)-1,3,5-triazin-2,4,6 (1H, 3H, 5H)-trione, bis (4-tert.-butyl-3-hydroxy-2,6-dimethylbenzyl)dithiolterephthalate, tris (3,5-ditert.-butyl-4-hydroxybenzyl) isocyanurate, the triester of β-(4-hydroxy-3,5-ditert.-butylphenyl) propionic acid with 1,3,4-tris-(2-hydroxyethyl)-5-triazin-2,4,6 (1H, 3H, 5H)-trione, bis [3,3-bis-(4′-hydroxy-3-tert.-butylphenyl)-butyric acid] glycol ester, 1,3,5-trimethyl-2,4,6 tris-(3,5-ditert.-butyl-4-hydroxybenzyl) benzene, 2,2′-methylene-bis-(4-methyl-6-tert.-butylphenyl) terephthalate, 4,4-methylene-bis-(2,6-ditert.-butyl-phenol),4,4′-butylidene-bis-(tert.-butyl-meta-cresol), 4,4-thio-bis-(2-tert.-butyl-5-methyl-phenol), 2,2′-methylene-bis-(4-methyl-6-tert.-butyl-phenol.

Sulphur-containing antioxidative co-stabilizers which may be used include for example distearylthiodipropionate, dilaurylthiodipropionate, methane tetrakis (methylene-3-hexylthiopropionate), methane tetrakis (methylene-3-dodecylthiopropionate) and dioctadecyl-disulphide. Phosphorus-containing co-stabilizers include for example trinonylphenyl phosphite,4,9-distearyl-3,5,8,10-tetraoxadiphosphaspiroundecane, tris-(2,4-ditert.-butylphenyl)phosphite and tetrakis (2,3-ditert.-butylphenyl)-4,4′-biphenylene diphosphonite. Further additives such as aminoaryl compounds and UV-absorbers and light stabilizers e.g. 2-(2′-hydroxyphenyl)benzotriazole, 2-hydroxybenzophenone, 1,3-bis-(2′-hydroxybenzyl) benzene, salicylates, cinnamates, benzoates and substituted benzoates, sterically hindered amines and oxalic acid diamides may be used. Other known types of additives, e.g. flame retardants and antistatic agents, may also be added.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 100° C., in order to harden the finish in an acceptable time once it has been applied to the primer-coated metal surface. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminum, in order to provide optical effects due to reflection. Such finishes are often two-coat finishes, in which a clear top coat is applied over a base coat containing the pigment and metal flakes. Such two-coat metallic finishes have particular need of UV stabilizers in the top coat, since the polymer in this coat is not protected by light-absorbing pigments, and it is subjected to almost double the normal amount of radiation because of reflection of light from the lower metallic layer.

The compounds of formula I are particularly useful in stoving finishes, particularly in the top coat of two-layer metallic finishes.

The compounds of formula I are suitable for use as UV stabilizers in a wide range of liquid finishes, for example those based on combinations of melamine-formaldehyde resins with oil-modified polyester resins, polyacrylate resins with added cross-linkers, or saturated polyesters; or on self-crosslinked polyarylate or polyacrylate resin copolymerised with styrene.

Further examples are two-component finishes based on an aliphatic or aromatic di-isocyanate and a hydroxy-group-containing polyacrylate, polyester or polyether resin. Thermoplastic polyarylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates.

The compound of formula I may be added to the finish at any stage in its manufacture, and may be added in solid form or in solution, preferably in the form of a liquid concentrate in a suitable solvent.

The addition of from 0.02–5% by weight, preferably 0.2–2% by weight of one or more compounds of formula I gives a clear improvement in the light- and weather-stability of organic pigments in stoving finishes as well as reducing the tendency to hairline cracking and loss of gloss as the result of weathering. This is surprisingly also found for metallic finishes, and excellent long-term stability of the clear top coat of two-layer metallic finishes is obtained. In such finishes, the compound of formula I may be added to the metallic undercoat, the clear top coat or both, preferably only to the clear top coat.

The following Examples, in which all part are by weight and all temperatures in degrees centigrade, illustrate the invention.

EXAMPLE 1

(a) To a solution of 91 parts 4-hydroxy-2,2,6,6-tetramethylpiperidine in 180 parts ethanol at 70° is added over 1 hour 71 parts of a 70% solution of glycollic acid nitrile, and the mixture is stirred for 12 hours at 70°. The ethanol is removed by vacuum distillation and the residue is treated with toluene at 80°. The toluene-soluble part is separated and cooled, whereupon the compound of formula II

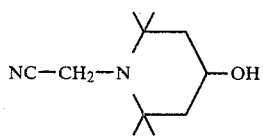

separates as crystals m.p. 119°–121°.

(b) 4 Parts of the compound of formula II, above, is dissolved in 50 parts tetrahydrofuran (THF) containing 2 parts ammonia, and 1 part of a catalyst consisting of 5% rhodium on alumina is added. Hydrogenation is carried out at 60°, 50 at. pressure for 5 hours, and the solvent is finally removed by distillation leaving a residue of compound No. 1 of Table 1. Recrystallisation gives pure material of m.p. 96°–98°.

EXAMPLE 2

A mixture of 4 parts of the compound of Example 1, 2 parts of acetic anhydride and 30 parts ether is stirred for 24 hours at 25°. The reaction mixture is neutralized with dilute caustic soda; cooled to 0° and filtered by suction. The solid residue is dried at 60°, 20 torr and finally purified by column chromatography on silica gel with ethanol/conc.ammonia (100:1) as eluent. Compound 2 of Table 1 is obtained.

EXAMPLE 3

A solution of 2.4 parts of the compound of Example 2 in 40 parts THF is treated with 0.76 parts LiAlH$_4$ at 25° and then stirred for 24 hours under reflux. After cooling to 10°, 10 parts water are slowly added dropwise, and the mixture is stirred for a further half hour. The resulting precipitate is filtered and washed with THF. After removal of THF from the filtrate and washings by vacuum distillation, the residue gives compound 3 of Table 1 as white crystals.

EXAMPLE 4

2.2 Parts of the compound of Example 1, 20 parts ether and 10 parts 1 N caustic soda are shaken in a separating funnel with 1.5 parts benzoyl chloride. A white precipitate is formed, which is filtered and washed with either. Recrystallization from acetone gives compound 4 of Table 1 as white crystals.

EXAMPLE 5

To a stirred mixture of 5.3 parts of the compound of Example 1, 100 parts ether, 15 parts water and 27 parts 1N caustic soda is added over 15 minutes 3.2 parts sebacic acid dichloride. The resulting white precipitate is filtered and dried to give compound No. 5 of Table 1 as white crystals.

EXAMPLE 6

The compound of Example 5 (5 parts) is refluxed for 48 hours with 2.7 parts LiAlH$_4$ in 100 parts THF. After careful addition of 25 parts water at 0°, the resulting suspension is suction filtered and washed repeatedly with ether. The solvent is removed from the filtrate and washings. The residue is purified by recrystallisation from acetone and column chromatography (silica gel, ethanol/conc. ammonia 10:1), giving compound No. 6 of Table 1.

EXAMPLE 7

A mixture of 50 parts acetone, 3.7 parts cyanuric chloride and 8 parts of the compound of Example 1 is warmed to 35°. A solution of 1.6 parts NaOH in 10 parts water is added dropwise over 15 minutes, and the reaction mixture is stirred for 6 hour at 35°. The resulting mixture is poured into 200 parts water, the resulting white precipitate is suction filtered, washed with water and recrystallized from acetone/water to give compound 7 of Table 1.

EXAMPLE 8

A mixture of 4 parts of the compound of Example 7, 1.6 parts of the compound of Example 1, 0.3 parts powdered NaOH and 30 parts toluene is boiled under reflux for 23 hours. On cooling to 0°, a precipitate forms which is suction filtered, washed with water and dried to give compound No. 8 of Table 1.

EXAMPLES 9 AND 10

In analogy to Example 7 and with suitable choice of starting materials, compounds 9 and 10 of Table 1 are obtained.

EXAMPLE 11

A mixture of 1.4 parts of the compound of Example 3, 1.7 parts 2-chloro-4,6-bispiperidino-1,3,5-triazine, 0.25 parts powdered NaOH and 30 parts toluene is stirred under reflux for 48 hours. The reaction mixture is cooled and filtered, and the filtrate evaporated in vacuo. The residue is purified by column chromatography and recrystallised from ethyl acetate, giving compound 11 of Table 1.

EXAMPLE 12

A mixture of 2.7 parts of the compound of Example 1, 1.5 parts triethylamine and 100 parts toluene is stirred and treated at 0° with a solution of 3.6 parts 3-(4-hydroxy-3,5-di-t.-butyl)phenylpropionyl chloride in 30 parts toluene. The mixture is stirred for 24 hours at 25°, and the resulting white precipitate suction filtered. The filtrate is evaporated and the residue purified by column chromatography and recrystallisation from hexane to give compound No. 12 of Table 1.

EXAMPLE 13

A mixture of 4 parts of the compound of Example 1, 5.8 parts 3-(4-hydroxy-3,5-di-t.-butyl)phenylpropionic acid methyl ester and 0.2 parts sodium hydride in 30 parts xylene is refluxed for 4 hours. After filtration, evaporation and purification by column chromatography and recrystallisation from hexane, compound 13 of Table 1 is obtained.

EXAMPLE 14

To a mixture of 11.1 parts 3-(4-hydroxy-3,5-di-t.-butyl)-phenylpropionic acid, 8.2 parts dicyclohexylcarbodiimide and 0.6 parts 4-pyrrolidinopyridine in 150 parts chloroform is added dropwise at 25° a solution of 4 parts of the compound of Example 1 in 25 parts chloroform. After stirring 26 hours, filtration, evaporation and purification as in Example 13, compound 14 of Table 1 is obtained.

EXAMPLE 15

A mixture of 0.8 parts of the compound of Example 1, 3.7 parts stearoyl chloride and 20 parts toluene is refluxed for 1 hour. After cooling to 20°, excess acid chloride is reacted with methanol and the reaction mixture brought to pH 10 with 2 N caustic soda. Filtration and workup of the filtrate gives compound 15 of Table 1.

EXAMPLE 16

A mixture of 1.7 parts hexamethylenediisocyanate and 20 parts ether is stirred under nitrogen and reacted at room temperature with a solution of 2 parts of the compound of Example 1 in 30 parts toluene/ether (1:2). A white precipitate is obtained, which after 4 hours is separated and washed with ether to give compound No. 16 of Table 1.

EXAMPLE 17

By analogy with Example 15, but starting with the compound of Example 6, compound 17 of Table 1 is obtained.

TABLE 1

Compounds of formula

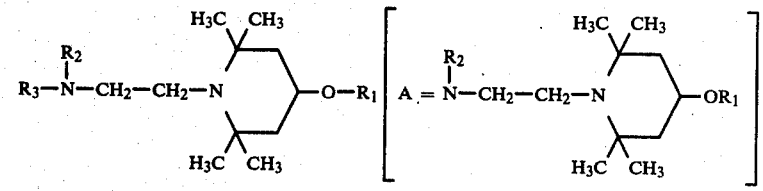

| No. | $R_1$ | $R_2$ | $R_3$ | m.p. °C. |
|---|---|---|---|---|
| 1 | H | H | H | 96–98 |
| 2 | H | −C(=O)−CH$_3$ | H | 138–140 |
| 3 | H | H | −C$_2$H$_5$ | 135–136 |
| 4 | H | −C(=O)−Ph | H | 156–157 |
| 5 | H | H | −C(=O)−(CH$_2$)$_8$−C(=O)−A | 193–196 |
| 6 | H | H | −(CH$_2$)$_{10}$−A | 162–163 |
| 7 | H | H | triazine with Cl, Cl substituents | 190–193 |
| 8 | H | H | triazine with A, A substituents | 198–200 |
| 9 | H | H | triazine with Cl, piperidinyl substituents | 138–140 |
| 10 | H | H | triazine with two piperidinyl substituents | 178–180 |
| 11 | H | C$_2$H$_5$ | " | 145–146 |

TABLE 1-continued

Compounds of formula

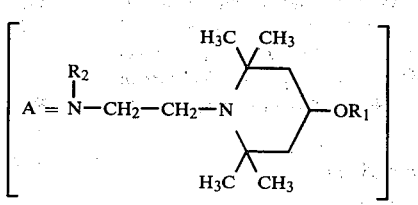

| No. | R₁ | R₂ | R₃ | m.p. °C. |
|-----|-----|-----|-----|----------|
| 12 | H | H | 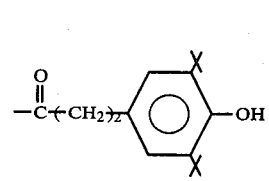 | 70–72 |
| 13 | 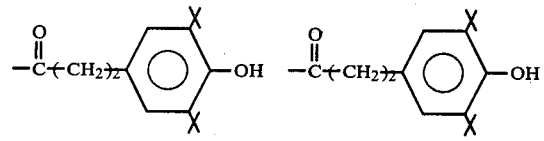 | H | H | 95–97 |
| 14 | 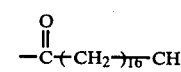 | 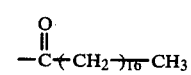 | H | 85–86 |
| 15 | $-\overset{O}{\underset{\|}{C}}{+}CH_2{\rightarrow}_{16}CH_3$ | $-\overset{O}{\underset{\|}{C}}{+}CH_2{\rightarrow}_{16}CH_3$ | H | 77–79 |
| 16 | H | H | $-\overset{O}{\underset{\|}{C}}-NH{+}CH_2{\rightarrow}_6 N{=}C{=}O$ | 58–62 |
| 17 |  | | | 38–40 |

Application Example A 0.5% by weight of the compound of Example 15 is worked into polypropylene (containing no UV stabilizer) in a kneading mixer at 180°. The resulting mass is pressed into a 3 mm thick plate, and also into a 0.3 mm thick film. The film is illuminated in an Atlas Weatheromether WRC 600 with a xenon lamp, and the damage caused by UV light is measured by the growth in intensity of the IR carboxyl band absorption at 5.8μ. According to test method DIN 53453, the change in impact strength of samples cut from the 3 mm plate is measured after exposure in the Atlas Weatherometer. In both cases the results obtained are better than those using unstabilized polymer.

Application Example B

A two-layer metallic finish is prepared having the following composition:
(a) base coat 12.6 parts commercial polyacrylate resin, with added cross-linking as defined in DIN 53 186 (Viacryl SC 344, Vianova, Vienna, supplied as 50% solution in xylene/butanol 4:1)
2.19 parts commercial butanol-etherified melamine resin, medium reactive, prepared by condensation of 1 mole melamine with 3–6 moles formaldehyde, etherified with 3–6 moles butanol according to DIN 53 187 (Maprenal MF 800, Casella, supplied as 72% solution in isobutanol)
0.96 parts butanol
0.26 parts colloidal silicic acid
7.05 parts xylene
52.0 parts of a 20% cellulose acetate butyrate solution of the following composition by weight:
  20% cellulose acetate butyrate; acetyl content 13.6%, butyryl content 38.7%, hydroxyl content 1.25%, viscosity of 20% solution in acetone=200 cp
  10% butanol
  35% xylene 35% butyl acetate 6.80 parts non-leafing aluminum paste, supplied as 65% suspension in alkylglycol acetate according to DIN 55 923

18.14 parts butyl acetate 0.3 parts copper phthalocyanine blue (C.I. Pigment Blue 15:1)

(b) top coat 80.00 parts polyacrylate resin (as in the base coat)

13.75 parts melamine resin (as in the base coat)

4.50 parts butyl glycollate 7.50 parts aromatic hydrocarbon solvent, b.p. 186°–212°

6.00 parts aromatic hydrocarbon solvent, b.p. 155°–178°

(c) application

The base coat is applied to primer-coated metal plates by spraying, giving a layer approx. 20 μm thick, without UV stabilizer. After drying of the base coat, the plates are sprayed with (i) top coat as in (b) above, without UV stabilizer or (ii) top coat as in (b) above, containing 1 part (i.e. 1% by weight) of the compound of Example 15, added as an 80% solution in xylene, and stoved at 140° for 30 minutes. Exposure tests (1 year in Florida) show superior results for the plates coated with top coat ii).

The compounds of Example 1–14, 16 and 17 can be used in analogous manner to Application Examples A and B.

What is claimed is:

1. A compound of formula I

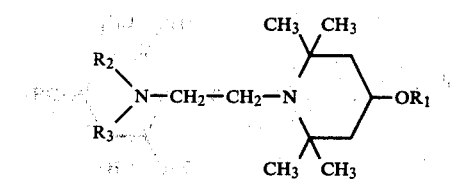

I in which $R_1$ is hydrogen or a group

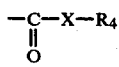

(a)

in which

X is a direct bond, —O— or —NH—; and $R_4$ is $C_{1-18}$alkyl, $C_{5-8}$cycloalkyl, phenyl ($C_{1-4}$) alkyl, phenyl, phenyl substituted with 1 or 2 $C_{1-12}$alkyl groups having together no more than 18 carbon atoms, or the group

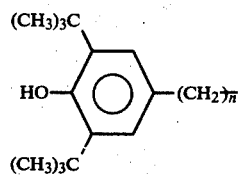

(e)

in which n=0, 1 or 2, or, when X is —NH—, $R_4$ may also be $C_{1-18}$alkyl monosubstituted by isocyanate $R_2$ is hydrogen, $C_{1-18}$alkyl or a group (a); and $R_3$ is hydrogen, $C_{1-18}$alkyl or a group (b), (c) or (d)

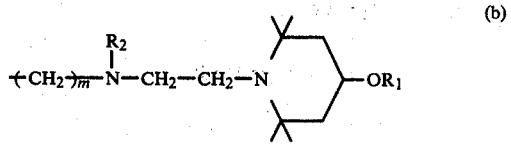

(b)

in which m is 2-10 and $R_1$ and $R_2$ are as defined above,

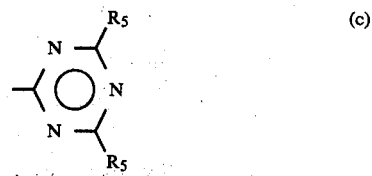

(c)

in which each $R_5$ independently is chlorine;

(f)

in which $R_7$ is hydrogen, $C_{1-18}$alkyl or β-hydroxyethyl and $R_8$ is $C_{1-18}$alkyl, β-hydroxyethyl or phenyl or $R_7$ and $R_8$ together with the nitrogen atom to which they are attached form a piperidine or morpholine ring;

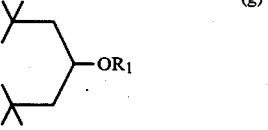

(g)

in which $R_2'$ is hydrogen or $C_{1-18}$alkyl and $R_1$ is as defined above;

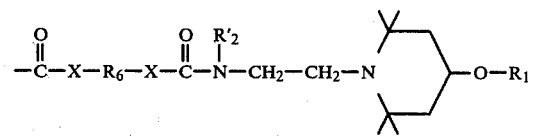

(d)

in which

X, $R_1$ and $R_2'$ are as defined above, and $R_6$ is $C_{2-10}$alkylene, phenylene, phenylene mono- or di-substituted by $C_{1-9}$alkyl, or, when X is a direct bond, $R_6$ may also be —CH$_2$— or a direct bond, provided that, when $R_3$ is a group (c) or (d) then $R_2$ is $R_2'$; or $R_2$ and $R_3$, together with the nitrogen atom to which they are attached, form a succinimide, maleimide or phthalimide ring.

2. A compound according to claim 1 of formula Ia

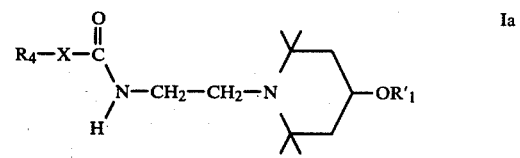

Ia in which X and $R_4$ are as defined in claim 1, and $R_1'$ is hydrogen or a group

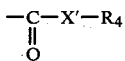

in which X' is a direct bond or —NH—.

3. A compound according to claim 2 of formula Ia'

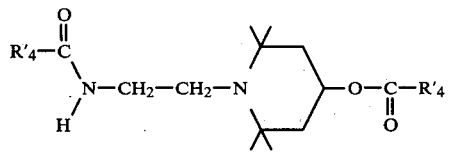

in which $R_4'$ is $C_{1-18}$alkyl, cyclohexyl, benzyl or phenyl.

4. A compound according to claim 1 of formula Ib

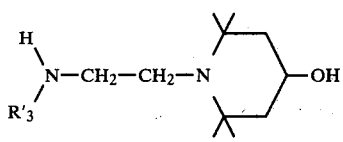

in which $R_3'$ is $C_{1-18}$alkyl or a group (c) or (d) defined in claim 1.

5. The compound of formula Ic

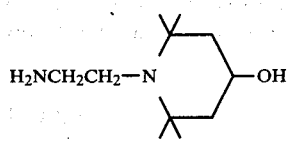

6. A process for the stabilization of polymeric materials against the effect of light comprising the incorporation of from 0.01 to 5% by weight of a compound of claim 1, into the polymeric material to be stabilized.

7. A polymeric material stabilized against the effects of light, containing from 0.01 to 5% by weight of a compound of claim 1.

8. A solid masterbatch composition containing 20-80% by weight of a compound of claim 1 and 80-20% by weight of a solid thermoplastic polymer.

9. A liquid stoving automotive finish for application to a metal surface, containing 0.02-5% by weight of a compound of claim 1.

10. A cured automotive finish obtained by applying and stoving a liquid finish according to claim 9.

11. The compound of claim 1 in which $R_1$ and $R_3$ are hydrogen atoms and $R_2$ is

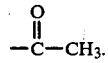

12. The compound of claim 1 which has the formula:

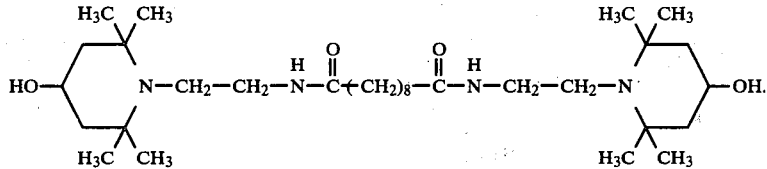

13. The compound of claim 1 which has the formula:

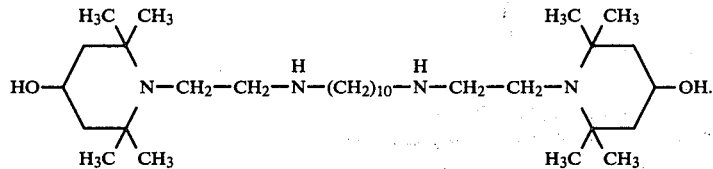

* * * * *